US011344701B2

(12) United States Patent
Andersin et al.

(10) Patent No.: US 11,344,701 B2
(45) Date of Patent: May 31, 2022

(54) URINARY CATHETER ASSEMBLY WITH ATTACHABLE HANDLE

(71) Applicant: DENTSPLY IH AB, Mölndal (SE)

(72) Inventors: Per Andersin, Mölnlycke (SE); Karsten Eriksson, Fotö (SE); Isak Folenius, Gothenburg (SE); Michael Sandberg, Askim (SE)

(73) Assignee: DENTSPLY IH AB, Mölndal (SE)

( * ) Notice: Subject to any disclaimer, the term of this patent is extended or adjusted under 35 U.S.C. 154(b) by 409 days.

(21) Appl. No.: 16/421,252

(22) Filed: May 23, 2019

(65) Prior Publication Data

US 2019/0358435 A1    Nov. 28, 2019

(30) Foreign Application Priority Data

May 24, 2018    (EP) .................................... 18174049

(51) Int. Cl.
*A61M 25/01*    (2006.01)
*A61M 25/00*    (2006.01)

(52) U.S. Cl.
CPC ...... *A61M 25/0136* (2013.01); *A61M 25/002* (2013.01); *A61M 25/0009* (2013.01); *A61M 25/0017* (2013.01)

(58) Field of Classification Search
CPC .......... A61M 25/0136; A61M 25/0009; A61M 25/0017; A61M 25/002;

(Continued)

(56) References Cited

U.S. PATENT DOCUMENTS

| 5,217,114 A | 6/1993 | Gadberry et al. |
| 5,653,700 A | 8/1997 | Byrne et al. |
| (Continued) | | |

FOREIGN PATENT DOCUMENTS

| CA | 165542 | 10/1915 |
| CA | 153020 | 9/2014 |
| (Continued) | | |

OTHER PUBLICATIONS

European Search Report for European Patent Application No. 18174049.9, dated Dec. 5, 2018 (9 pages).

(Continued)

*Primary Examiner* — Quang D Thanh
*Assistant Examiner* — Brandon W. Levy
(74) *Attorney, Agent, or Firm* — Perkins Coie LLP (57) ABSTRACT

A urinary catheter assembly comprises: a urinary catheter, a tubular case and a sleeve fixedly arranged over at least a part of a non-insertable section of the urinary catheter. The sleeve includes two oppositely arranged openings and a body extending between the opening. In a first position, a storage position, the tubular case is arranged to enclose the insertable section of the urinary catheter and is removably connected to the sleeve and/or to the non-insertable section of the urinary catheter. The body portion of the sleeve is provided with a first engagement member, and the tubular case is provided with a second engagement member, thereby enabling the tubular case, when removed from the non-insertable part of the urinary catheter, to be releasably connected to the sleeve in a second disposition, the second disposition being different from the first disposition. A method for producing a urinary catheter assembly is also disclosed.

18 Claims, 5 Drawing Sheets

(58) Field of Classification Search
CPC ...... A61M 2210/1089; A61M 25/0111; A61M 25/01; A61M 25/0045; A61M 2025/0046; A61M 2210/1085; A61M 27/008; A61M 2202/0496; A61M 2205/04; A61M 2210/1096

See application file for complete search history.

(56) References Cited

U.S. PATENT DOCUMENTS

| | | | |
|---|---|---|---|
| 6,063,063 A * | 5/2000 | Harboe | A61F 2/0009 604/256 |
| D478,383 S | 8/2003 | Timm et al. | |
| D561,461 S | 2/2008 | Smetham et al. | |
| D588,797 S | 3/2009 | Tanghoej et al. | |
| 7,682,353 B2 | 3/2010 | Tanghoj et al. | |
| D614,396 S | 4/2010 | Tanghoej et al. | |
| 7,867,220 B2 | 1/2011 | Tanghoj | |
| 8,398,615 B2 | 3/2013 | Torstensen et al. | |
| 8,491,533 B2 | 7/2013 | Parihar et al. | |
| D692,998 S | 11/2013 | Broberg et al. | |
| D705,925 S | 5/2014 | Murray et al. | |
| D748,782 S | 2/2016 | Zhang et al. | |
| D759,813 S | 6/2016 | Newman et al. | |
| D764,657 S | 8/2016 | Bokelman et al. | |
| D770,611 S | 11/2016 | Saussaye et al. | |
| D775,723 S | 1/2017 | Rowe et al. | |
| D779,059 S | 2/2017 | Nino | |
| D789,075 S | 6/2017 | Hannon et al. | |
| D809,778 S | 2/2018 | Hannon et al. | |
| D810,282 S | 2/2018 | Ratjen | |
| D815,737 S | 4/2018 | Bergström et al. | |
| D817,483 S | 5/2018 | Falleboe et al. | |
| D820,583 S | 6/2018 | O'brien et al. | |
| D828,011 S | 9/2018 | O'Brien et al. | |
| 10,076,636 B2 | 9/2018 | Murray et al. | |
| D837,974 S | 1/2019 | Hannon et al. | |
| 10,166,366 B2 | 1/2019 | Murray et al. | |
| D840,145 S | 2/2019 | Lucciola | |
| D841,155 S | 2/2019 | McMenamin et al. | |
| D846,116 S | 4/2019 | Naughton et al. | |
| 10,561,817 B2 | 2/2020 | Hannon et al. | |
| D910,836 S | 2/2021 | Sandberg et al. | |
| 11,020,561 B2 | 6/2021 | O'brien et al. | |
| 2004/0158231 A1 * | 8/2004 | Tanghoj | A61M 25/01 604/544 |
| 2006/0142737 A1 | 6/2006 | Tanghoj | |
| 2012/0197200 A1 | 8/2012 | Belson | |
| 2016/0067445 A1 | 3/2016 | Murray et al. | |
| 2017/0173300 A1 | 6/2017 | Hannon et al. | |
| 2017/0291011 A1 | 10/2017 | McMenamin et al. | |

FOREIGN PATENT DOCUMENTS

| | | | |
|---|---|---|---|
| CA | 171154 | 5/2017 | |
| CA | 171155 | 5/2017 | |
| CA | 176073 | 2/2018 | |
| CN | 99324216.2 | 1/1999 | |
| EM | 000248877-0001 | 5/2004 | |
| EM | 000248877-0003 | 5/2004 | |
| EM | 000248877-0004 | 5/2004 | |
| EM | 000563432-0001 | 7/2006 | |
| EM | 002306514-0001 | 9/2013 | |
| EM | 002306514-0002 | 9/2013 | |
| EM | 002879445-0002 | 11/2015 | |
| EM | 003418706-0001 | 10/2016 | |
| EM | 005247723-0002 | 4/2018 | |
| EM | 005247723-0003 | 4/2018 | |
| EP | 0093093 | 3/1986 | |
| EP | 0217771 | 12/1991 | |
| EP | 1090656 | 5/2004 | |
| EP | 2292294 A1 * | 3/2011 | ........ A61M 25/0014 |
| EP | 2686054 | 1/2014 | |
| GB | 2150836 | 7/1985 | |
| WO | 2003002179 | 1/2003 | |
| WO | 2003092779 | 11/2003 | |
| WO | 2004050155 | 6/2004 | |
| WO | WO-2011019359 A1 * | 2/2011 | ........ A61M 25/0014 |
| WO | 2014142917 | 9/2014 | |
| WO | 2014142930 | 9/2014 | |
| WO | 2015075841 | 5/2015 | |
| WO | 2015184365 | 12/2015 | |
| WO | 2016044379 | 6/2016 | |
| WO | 2016206701 | 12/2016 | |
| WO | 2017185029 | 10/2017 | |
| WO | 2017185052 | 10/2017 | |

OTHER PUBLICATIONS

European Search Report for European Patent Application No. 19159723.6, dated Aug. 20, 2019 (9 pages).

* cited by examiner

URINARY CATHETER ASSEMBLY WITH ATTACHABLE HANDLE

CROSS REFERENCE TO RELATED APPLICATIONS

This patent document claims the benefits and priority of European Patent Convention Application No. 18174049.9, filed on May 24, 2018, which is incorporated herein by reference in its entirety.

FIELD OF THE INVENTION

The present invention relates to a urinary catheter assembly. The invention is particularly related to hydrophilic catheters, and specifically to hydrophilic urinary catheters. The invention is also related to methods for producing and using such an assembly.

BACKGROUND

The disclosed technology relates to a urinary catheter assembly. Urinary catheters are commonly used for draining urine from the bladder. Urinary catheters can be of an indwelling type, for long term use, such as days or even weeks, or for intermittent use, whereby the catheters are used for a single draining procedure, typically lasting a few minutes. Intermittent urinary catheters are e.g. used by a large group of persons for self-catheterization, which is a daily-life procedure, taking place several times a day. Typically, catheters for intermittent catheterization are used by patients suffering from urinary retention, due to e. g. spinal cord injury, Multiple Sclerosis or Prosthatic Hyperplasia. Using an intermittent catheter, the bladder may be drained through a natural or artificial urinary canal. Many catheters, such as those for intermittent catheterization, are provided with a hydrophilic coating or the like, providing a smooth and slippery surface when wetted, for safe and comfortable insertion in the urinary canal.

Individuals who suffer from urinary incontinence will normally self-catheterize several times a day. Self-catheterization involves removing the catheter assembly from its package and inserting and advancing the catheter tube through the user's urethra. However, preparation and manipulation of known catheter assemblies is often complicated and tedious. Further, often users of intermittent urinary catheters have limited or diminished dexterity, e.g. as a result of spinal cord injuries. Also, users of intermittent catheters are often required to self-catheterize outside the privacy of the home, such as in public restrooms. Thus, for these and other reasons, it is desirable that the intermittent catheters are provided in discrete packaging that is easy to open and manipulate, which are compact and portable, and wherein the catheter can be deployed and used in a way that alleviates concerns about inadvertent urine leakage or spillage and avoids pain or discomfort to the user.

Many attempts to obtain this have been made in the past. For example, WO 03/092779 proposes a urinary catheter assembly in which a package is connected to a flared connector of the catheter, thereby providing a small package, where the connector is at least partly exposed to the environment and forms part of the package. Similar solutions are disclosed in WO 2014/142917 and WO 2015/184365. Another example is disclosed in WO 2016/044379, in which the package can be connected to the rear end of the connector of the catheter, to function as a handle. However, all of these known assemblies are relatively difficult to use and prepare for use, and are also relatively complicated and costly to produce.

Thus, there is still a need for improved urinary catheter assemblies. The assembly should preferably be relatively simple and cost-efficient to produce. Further, the assembly should be easy and intuitive to open and use, even for users with reduced dexterity. The assembly should also preferably be rather small, so that it can easily be carried around by the user in his/her daily life.

SUMMARY

It is therefore an object of the present invention to provide a urinary catheter assembly which at least alleviates the above-discussed problems.

This object, and other features and benefits, are obtained based on the disclosed embodiments including by means of a urinary catheter assembly and a method in accordance with the appended claims.

According to a first aspect of the disclosed embodiments there is provided a urinary catheter assembly comprising:

a urinary catheter having an insertable section and a non-insertable section;

a tubular case provided with a closed end and an open end; and a sleeve fixedly arranged over at least a part of the non-insertable section of the urinary catheter, the sleeve including two oppositely arranged openings and a body portion extending between said openings;

wherein the tubular case, in a storage position, is arranged to enclose the insertable section of the urinary catheter and removably connected to the sleeve and/or to the non-insertable section of the urinary catheter, wherein the tubular case is in a first disposition in relation to the sleeve, and wherein the body portion of the sleeve is provided with a first engagement member, and wherein the tubular case is provided with a second engagement member, thereby enabling the tubular case, when removed from the non-insertable part of the urinary catheter, to be releasably connected to the sleeve in a second disposition, the second disposition being different from the first disposition.

In accordance with the disclosed embodiments, the tubular case serves two purposes. It functions as a package, for maintaining at least the insertable section of the catheter in a clean and sterile condition during storage, prior to use. When the catheter is a hydrophilic catheter, the case may also accommodate a wetting fluid for activation of the hydrophilic catheter, and preferably for maintaining the catheter continuously wetted and activated during storage. In particular, the wetting fluid may be arranged in direct contact with the catheter during storage. The package can also be resealable, allowing the catheter to be reinserted into the package after use, and preferably to be closable once the catheter has been reinserted. However, the tubular case also functions as a handle, when in the second disposition, for allowing convenient and effective gripping and handling of the catheter during use, which is of particular importance for users having reduced or poor dexterity. Hereby, a relatively large gripping area is provided, allowing the user to use a multifold various positions and techniques for handling the catheter. A user may e.g. grip the handle provided by the case with the entire hand, in a palmar grip, a position which is very useable in particular for users having poor dexterity. However, the handle may also be gripped by the use of only the fingers, such as two or three fingers, e.g. in a traditional pencil grip, a drumstick grip, a paint brush grip, a cross thumb grip or the like. Thus, the handle is very versatile, allowing to be gripped in any suitable position.

Further, the tubular case is relatively long. The case preferably has an elongate shape, and preferably has a length which at least exceeds the length of the insertable part of the catheter shaft. The catheter assembly may be for female use. The female urethra is normally about 5 cm long, and thus the length of the insertable part of the catheter shaft is preferably 4-10 cm long. Correspondingly, the tubular case preferably has a length in the range of 5-15 cm, and preferably in the range 8-12 cm. Due to the relatively long length of the tubular case, the user may choose whether to grip the handle close to the catheter, or some distance away from the catheter. This is particular advantage, since users may have difficulty in reaching too far down. Further, many users would also prefer to handle the catheter from above, without e.g. having to reach down below the rim of the toilet bowl.

This function is further enhanced when the tubular case when in the second disposition assumes an angularly displaced position in relation to the longitudinal direction of the catheter, so that it extends laterally from the catheter.

Further, for users and situations where an enlarged handle is not necessary, the catheter may still be used without attaching the tubular case to the sleeve. This makes the new catheter assembly even more versatile.

Still further, opening of the assembly, withdrawal of the catheter, connection of the tubular case to the sleeve to serve as a handle, and reinsertion of the catheter into the tubular case after use, to reseal the assembly, is easily understandable in an intuitive way, facilitating opening and use of the assembly also for inexperienced users.

Thus, the catheter assembly provides a compact and neat storage position, when the tubular case is in the first disposition. In this position, the catheter assembly could easily be carried around discretely, e.g. in a handbag, in a pocket or the like, without attracting notice. Further, due to the engagement surfaces, the catheter assembly can easily be transformed into the use position, in which the tubular case is connected to the sleeve in the second disposition, so that it e.g. extends out laterally as a handle, for convenient use, as discussed in the foregoing. After use, the catheter assembly may be directly discarded. However, it may alternatively be returned to the closed storage position, so that the used catheter assembly can then be carried by the user in the same discrete way as the unopened assembly, and without the risk of spillage etc. to be discarded later.

The urinary catheter assembly is preferably elongate, and preferably having an essentially circular cross-sectional shape. However, other shapes, such as a rectangular or oval cross-sectional shape are also feasible. The overall appearance of the urinary catheter assembly may e.g. be similar to that of a pen.

In the second disposition, the tubular case preferably extends in an angular position in relation to the longitudinal direction of the catheter and/or the sleeve. Preferably, the angular position(s) is/are in the range exceeding 30 degrees and up to 120 degrees. Preferably, the angular range is 60-120 degrees, and more preferably 75-105 degrees, and even more preferably 80-100 degrees. In one embodiment, the angular position is about 90 degrees.

It is also feasible that the first and second engagement members are such that engagement in more than one way is possible, e.g. allowing the tubular case to be engaged in two or more different angular positions in relation to the sleeve. It is also possible to provide two or more first engagement members on the sleeve, each providing a different angular orientation of the tubular case when connected to the sleeve.

The catheter assembly is also cost-effective to produce, since it comprises relatively few, and easily producible parts. For example, the tubular case and sleeve may be produced by extrusion, injection molding or the like. Further, the catheter may be identical or similar to a conventional catheter, e.g. having a relatively straight inner lumen, etc. This allows the catheter to be produced in a conventional way, and thereafter be attached or included into the assembly. For example, the relatively straightly occurring inner lumen of the catheter, and the avoidance of any obstacles at or in the vicinity of the output area, i.e. close to the distal end, enables easy and convenient access into the catheter from the rear end during production. This is of great advantage e.g. when applying a coating to the catheter surface, when punching out drainage openings, thermoforming of the tip, etc.

The sleeve is fixedly connected to the non-insertable section of the catheter, meaning that the sleeve is not removable from the non-insertable section by the normal, intended handling of the catheter assembly. The fixed connection can e.g. be formed by a friction fit, but may also be formed by ultrasonic welding, adhesion or the like. The fixed connection can also be obtained already during manufacturing of the sleeve and the non-insertable section, e.g. by use of 2-component (2 k) injection molding.

To summarize, the urinary catheter assembly provides many advantages in relation to previously known catheter assemblies, such as a more cost-efficient production and assembling, ease to prepare the catheter for use, including intuitiveness to open, ease of opening, ease of removal of the catheter from the case, ease of handling the catheter during catheterization, ease of closing the case after use, improved compactness and reduced size, improved discretion, improved portability, improved cleanliness, reduced risk of spillage, improved hygiene, etc.

In the present application, the term "proximal" is used to indicate the end or portion of a catheter that is inserted into the body of the user, i.e. the end or portion of the catheter tube that during use is closer in proximity to the user's body and/or initially enters the user's body upon insertion. The term "distal" is used to refer to an end or portion of the catheter tube that is opposite the proximal end or portion and is typically further away from the user's body. For the sake of consistency, when the terms "distal" and "proximal" are used in the context of other components, such as the sleeve and the tubular case, which are not intended for introduction into the user's body. For such other components, "proximal" refers to the end or portion that is closer to the proximal end of the catheter tube when the catheter tube is housed within the assembly, while "distal" refers to an end or portion located opposite to such proximal end or portion.

The tubular case is, in the first position, removably attached to either the sleeve or the catheter, or both, providing a sealed enclosure within the case for at least the insertable section of the catheter during storage, thereby maintain the insertable section of the catheter in a clean and sterile state. The catheter and sleeve are removed from the case upon use, but are preferably reattachable to the case after use, thereby again providing a sealed compartment.

For example, the non-insertable section of the catheter may be provided with an enlarged part, e.g. forming part of a flared connector, which is insertable into the open end of the tubular case, and which forms a sealed closure in engagement with the inner wall of the tubular case.

The tubular case may together with the non-insertable section provide a sterile and moisture proof compartment for the insertable section of the catheter in the first disposition.

A seal member, such as a gasket or the like, e.g. in the form of an O-ring, may be provided between the tubular case and the catheter and/or the sleeve, such as being arranged around the catheter.

The non-insertable section of the catheter may include a flared connector portion, wherein the flared connector portion is at least partly accommodated within the sleeve.

In one embodiment, the flared connector portion has a length exceeding the length of the sleeve. In particular, the flared connector may extend out from the sleeve through at least one of the two oppositely arranged openings.

The first engagement member is preferably arranged on the body portion of the sleeve at a distance from both said oppositely arranged openings. The first engagement member may be arranged centrally on the sleeve body, but may additionally or alternatively be arranged close to one or both of the openings.

The second engagement member is preferably arranged at the closed end of the tubular case. However, additionally or alternatively, the second engagement member may be arranged at the open end of the tubular case.

The first engagement member is preferably at least one of an opening or recess in the body portion of the sleeve and a protrusion extending out from the body portion of the sleeve. The second engagement member preferably has a form and shape complementary to the form and shape of the first engagement member, thereby allowing the first and second engagement member to mate and connect to each other. Thus, one of the first and second engagement members may be in the form of an opening or recess, and the other may be in the shape of a protrusion, or the like, formed and dimensioned to be inserted into recess or opening. Also, more than one recess/opening and more than one protrusion may be provided, such as a two or three protrusions, arranged to be received in two or three corresponding openings, in a plug-and-socket type of connection. It is also feasible to have one or more protrusions arranged on each of the sleeve and the tubular case, and corresponding one or more openings/recesses on both of them.

However, other types of engagement members are also feasible, such as in the form of a latch, preferably with an undercut to form a tab, provided on one of the sleeve and the tubular case, and a corresponding slot arranged on the other of the sleeve and the tubular case, wherein the latch and the slot are engageable with one another; a detent provided on one of the sleeve and the tubular case, and a corresponding gap arranged on the other of the sleeve and the tubular case, wherein the detent and gap are engageable with one another; etc.

The first and second engagement members may be connectable through one of threads, a friction fit, a bayonet mount, a Luer connection, a snap-lock and a snap-fit arrangement.

The engagement surfaces of the first and second engagement members may be provided on outer surfaces of the first and second engagement members, such as outer surfaces of protrusions, stubs and the like, on inner surfaces of the first and second engagement members, such as inner surfaces of openings or recesses, or inner surfaces of hollow protrusions and the like, or on both inner and outer surfaces.

The first and second engagement members are arranged to attach the tubular case with the sleeve in such a way that the parts do not inadvertently fall apart. In other words, the first and second engagement members, when engaged, resist separation to a certain degree, thereby maintaining the parts together until deliberately brought apart.

The first and second engagement members are preferably complementary to each other in shape and/or size, thereby enabling engagement between the members. For example, one of the members may be slightly convex and the other slightly concave, or the surfaces may both be slightly conical or tapered.

In one embodiment, the second engagement member comprises a tapered, generally conical surface arranged at or in the vicinity of the closed end of the case.

One of the first and second engagement members are further preferably shaped and sized so that it may be inserted into the other of the first and second engagement member, so that an engagement surface is formed as an outwardly facing surface on the insertable, male part, and as an inwardly facing surface on the receiving, female part.

The first and second engagement members may form a friction fit connection. In a preferred embodiment, the first and second engagement members may comprise tapered, generally conical surfaces, having a corresponding shape, and arranged to be attached by means of a friction fit. Alternatively, the members may be arranged to be connected to each other by means of mechanical engagement, such as through a threading, a snap lock arrangement, or the like.

The compartment formed by the tubular case and accommodating the insertable section of the urinary catheter is preferably a closed, sealed compartment. To this end, it may be required to provide some type of closure for the catheter lumen, in case there are open inlet openings arranged within the compartment. Such a closure may be obtained in various ways. As one alternative, the inlet openings may be closed, e.g. by arranging the tip of the catheter, including these inlet openings, in a narrow part of the tubular case, thereby closing the inlet openings from the rest of the compartment, by arranging breakable or degradable membranes or the like over the inlet openings, etc. Such breakable or degradable membranes may additionally or alternatively be arranged anywhere along the length of the lumen, or at or in the vicinity of the outlet end. In case a degradable membrane is used, it may e.g. be arranged to degrade rapidly when in contact with urine or the like.

However, in a preferred embodiment, the catheter assembly may comprise an openable cap for closing a release opening at the non-insertable section of the urinary catheter. The cap may e.g. be connected to the catheter by means of a friction fit, a threaded connection or the like. In one exemplary embodiment, the cap is provided with a boss formed on the underside of the cap, and sized to fit into the opening of the release opening of the non-insertable section.

The cap may further be connected to the sleeve and/or the non-insertable section of the catheter via a hinge. Hereby, the cap remains in contact with the catheter assembly also when opened, which facilitates operation and avoids the need to handle and discard the cap separately. It also facilitates resealing of the catheter assembly after use, since the cap can hereby be restored into a closed state.

The hinge preferably provides a force to maintain the cap in an outwardly swiveled position when opened, thereby maintaining the cap out of the way for ordinary operation, and the release opening free and opened at all times. This may e.g. be accomplished by using a so called bi-stable living hinge.

The tubular case may further comprise a sloped or curved surface, and the sleeve may comprise a correspondingly sloped or curved surface which mates with the sloped or curved surface of the tubular case when in the storage position. The sloped or curved surface of the tubular case may e.g. be arranged at the rim of the open end, or as an outwardly or inwardly protruding flange or the like in the vicinity of the open end. The sloped or curved surfaces may facilitate removal of the catheter from the tubular case when in the storage position, by providing an axial force separating the sleeve and the tubular case from each other when the sleeve and the tubular case are rotated in relation to each other.

The catheter preferably comprises one or several drainage openings, so-called eyes, arranged at or in the vicinity of the proximal insertion end. At least the insertable section of the catheter may be provided with a hydrophilic coating, or in other ways been provided with a hydrophilic surface, which exhibits a lowered friction when wetted. Further, the distal section may, at least on a part thereof, have larger cross-sectional dimensions than the catheter shaft. The distal section may e.g. be flared or funnel shaped, increasing in dimension towards the distal end, thereby enabling connection of a tube, collection bag or the like.

The catheter may be a hydrophilic catheter, having a hydrophilic surface on at least the insertable section thereof. The hydrophilic surface may be arranged as a hydrophilic coating arranged on a substrate of the catheter, as is per se well known in the art. However, the hydrophilic surface may alternatively be arranged as an integrated part of the catheter, such as an integrated layer, or alternatively, the entire catheter, or part(s) of the catheter, may be made of a hydrophilic material. The hydrophilic surface is preferably arranged to provide low friction when wetted. The hydrophilic surface may be a surface provided with a hydrophilic coating, for example made in accordance with EP 0 093 093 and EP 0 217 771.

The catheter assembly may further comprise a wetting fluid, such as a wetting liquid, for wetting and activation of the hydrophilic surface. The wetting fluid may be arranged in a separate compartment within the assembly, to be released into the compartment housing the catheter shaft at a suitable time, such as immediately prior to use. However, the wetting fluid may also be provided within the same compartment as the insertable section of the catheter, and preferably in direct contact with the insertable section, thereby maintaining the catheter in a wetted, activated state also during storage. This wetted state may be present immediately following closing and sealing of the package, or be obtained after some time of storage. The activated state may thus be provided by pre-wetting of the catheter, prior to arrangement of the catheter in the package, but may alternatively be provided after placement of the catheter in the package. Specifically, wetting of the hydrophilic surface may occur during a period of storage in a sealed container by provision of a humid atmosphere in the package, as is per se known in the art, e.g. by being arranged within a hydration element, such as a chamber or sachet which is liquid impermeable and vapor permeable.

Since the hydrophilic surface is then maintained in a wetted state during storage, the medical device is immediately ready-to-use upon removal from the package, and need not be wetted or treated in any way prior to use.

The tubular case, and the compartment formed by the case, is preferably impermeable to the wetting fluid, and preferably made of a gas impermeable material. This ensures that moisture does not penetrate out from the package during storage, and enhances the shelf-life of the product.

Excess wetting fluid remaining in the tubular case when the catheter has been extracted from the tubular case may be discharged through the open end into a sink, a toilet bowl or the like. However, the wetting fluid may also be allowed to remain in the tubular case during the entire catheterization process. In particular when the second engagement member is located at the closed end of the tubular case, the tubular case can easily be maintained in an upright, vertical position at all times, both during extraction of the catheter from the case, during use of the case as a handle for catheterization, and when the catheter is reinserted into the case after use. Thus, it may in such an embodiment easily be ensured that any wetting liquid or the like stored within the package is not spilled, or at least that the risk of spillage is significantly lowered.

The catheter is preferably a urinary catheter for intermittent, short time use. The term "short term use" indicates a use that is limited in time, and in particular limited to a time period of less than 15 minutes, and preferably less than 10 minutes, and most preferably less than 5 minutes.

The wetting liquid is preferably an aqueous liquid, comprising at least 75% of weight of water, and preferably at least 80% of weight, and more preferably at least 85% of weight, and most preferably at least 90% of weight. In some embodiments, the wetting liquid may be plain water. However, the wetting liquid may also comprise one or more additives, such as an anti-bacterial agent, a pharmaceutical active substance, an osmolality increasing agent, or the like.

According to another aspect of the disclosed embodiments, there is provided a method for producing a urinary catheter assembly comprising:

providing a urinary catheter having an insertable section and a non-insertable section;

fixedly arranging a sleeve over the non-insertable section; and arranging at least the insertable section in a tubular case;

wherein the tubular case, in a storage position, is removably connected to the sleeve and/or to the non-insertable section of the urinary catheter, wherein the tubular case is in a first disposition in relation to the sleeve, and wherein the sleeve is provided with a first engagement member, and wherein the tubular case is provided with a second engagement member, thereby enabling the tubular case, when removed from the non-insertable part of the urinary catheter, to be releasably connected to the sleeve in a second disposition, the second disposition being different from the first disposition.

According to still another aspect of the disclosed embodiments, there is provided a method for preparing a urinary catheter assembly of the above-discussed type for use, the method comprising the steps:

remove the insertable section from the storage position in the tubular case;

bring the assembly from the first disposition to the second disposition;

connect, releasably, the first engagement member of the sleeve with the second engagement member of the tubular case; and using the tubular case as a handle for manipulation of the catheter when in the second disposition.

These and other aspects of the disclosed embodiments will be apparent from and elucidated with reference to the embodiments described hereinafter.

BRIEF DESCRIPTION OF THE DRAWINGS

For exemplifying purposes, the disclosed embodiments will be described in closer detail in the following with reference to embodiments thereof illustrated in the attached drawings, wherein.

DETAILED DESCRIPTION OF PREFERRED EMBODIMENTS

In the following detailed description preferred embodiments of the invention will be described. However, it is to be understood that features of the different embodiments are exchangeable between the embodiments and may be combined in different ways, unless otherwise specifically indicated. It may also be noted that, for the sake of clarity, the dimensions of certain components illustrated in the drawings may differ from the corresponding dimensions in real-life implementations of the invention, e.g. the length of the medical device, etc.

The urinary catheter assembly disclosed in relation to the illustrative example has an elongate, pen-like shape, and having a generally circular cross-section. However, as discussed in the foregoing the assembly may also have other shapes, such as being of a square, rectangular or oval shape.

The catheter assembly as illustrated in FIGS. 1-3C comprises a catheter 1 having an insertable section 11, forming a catheter shaft, and a non-insertable section 12, forming a connector part. The non-insertable section 12 preferably has a larger diameter than the insertable section 11. The rear end of the non-insertable section may be flared or funnel-shaped, and may be arranged to be connected to a tapered connection part of a urine collection bag or the like. It may also be connected to an extension tube, or be used for direct discharge of the urine into a toilet bowl or the like.

At least a part of the insertable section 11 forms an insertable length to be inserted through a urethra of the user.

The insertable section comprises an insertion tip, which may be a closed, rounded end. Further the insertable section may comprise inlet openings 13, so called catheter eyes or eyelets, leading into a lumen extending through the catheter, and into a discharge outlet 14 arranged at the rearward end of the non-insertable section.

The insertable section 11 may comprise a hydrophilic surface, and form a hydrophilic catheter, as is per se well known in the art. The hydrophilic surface may be in the form of a hydrophilic surface coating, for example PVP, and which provides a low-friction surface when wetted with a wetting fluid. Typically, the insertable length is within 50-140 mm for a female patient and 200-350 mm for a male patient. Even though PVP is the preferred hydrophilic material, other hydrophilic materials may be used, such as hydrophilic polymers selected from polyvinyl compounds, polysaccharides, polyurethanes, polyacrylates or copolymers of vinyl compounds and acrylates or anhydrides, especially polyethyleneoxide, polyvinyl-pyrrolidone, heparin, dextran, xanthan gum, polyvinyl alcohol, hydroxy propyl cellulose, methyl cellulose, copolymer of vinylpyrrolidone and hydroxy ethylmethyl acrylate or copolymer of polymethylvinyl ether and maleinic acid anyhydride. However, instead of a hydrophilic surface coating, the entire insertable section of the catheter may be formed of a hydrophilic material.

However, alternatively the catheter may be non-hydrophilic, and may e.g. be lubricated with gel prior to insertion.

The assembly further comprises a sleeve 2 being arranged over the entire or a part of the non-insertable section of the catheter. The sleeve 2 has a tubular shape, with a proximal opening 21 facing the insertable section of the catheter, a distal end 22 facing the opposite direction, and a tube body 23 extending between the openings. The sleeve is fixedly connected to the non-insertable section of the catheter. The fixed connection can e.g. be formed by a friction fit, but may also be formed by ultrasonic welding, adhesion or the like. The fixed connection can also be obtained already during manufacturing of the sleeve and the non-insertable section, e.g. by use of 2-component (2 k) injection molding. In the illustrative example, the non-insertable section of the catheter is provided with protruding rings 15a-c encircling the catheter, and assisting in forming a mechanical securing of the sleeve. These protruding rings 15a-c may e.g. interact with corresponding protruding or recessed parts on the inside of the sleeve body.

The enlarged, non-insertable section 12 of the catheter may extend out from the sleeve 2 through one or both openings 21, 22. In the illustrative example, the non-insertable section of the catheter 12 ends in the vicinity of the distal opening 22 of the sleeve. To this end, the catheter may extend out from the sleeve by a short length, such as 0.1-3 mm, as in the illustrative example, but may alternatively be flush with the opening, or end at a small distance beneath the opening, such as 0.1-3 mm.

At the other end, the enlarged, non-insertable section 12 of the catheter may extend out from the sleeve through the proximal opening 21 by a certain length, e.g. by 3-15 mm, and preferably by 3-5 mm. At this part protruding out from the sleeve through the opening 21, or inside the sleeve, but preferably relatively close to the opening 21, the non-insertable section 12 may further be provided with an annular gasket 16, such as an O-ring, to assist in forming a connection to a tubular case, to be discussed in more detail in the following. The gasket may e.g. be arranged in a circumferential groove arranged on the exterior surface of the catheter.

In the vicinity of the proximal opening 21, the sleeve may further be provided with threads or the like, to form a connection to the tubular case, again to be discussed in more detail in the following.

The assembly may further comprise a cap 3, to be arranged in the vicinity of the distal opening 22 of the sleeve. The cap may comprise a downwardly facing boss 31, arranged to extend into the outlet opening 14 of the catheter, and to form a sealed closure of the catheter lumen. In the illustrative example, the boss is formed as an annular downwardly protruding ring, but the boss may alternatively be formed like a disk, or assume other suitable shapes. The boss is preferably sized and shaped to fit within the outlet opening 14. The boss may also have a inwardly rounded edge, be conically tapered or the like, to fit more easily within the opening 14.

The cap may also comprise a downwardly protruding rim 32, arranged at certain distance outside the boss 31, and arranged to form a releasable connection with the catheter and/or the sleeve. Thus, the rim 32 is arranged to form a releasable, mechanical connection with the sleeve and/or the catheter, and in doing so ensures that the boss 31 comes in sealing engagement with the outlet opening 14 of the catheter. The mechanical connection may be formed by threads or the like, engaging with corresponding threads on the catheter and/or the sleeve, to form a twist-off cap.

However, the cap may also be connected by a friction connection, to form a flip-open cap, as shown in the illustrative example. A flip-open type of cap is very convenient and intuitive to use, since it resembles caps in many packages that are familiar to the ordinary user, such as toothpaste containers, ketchup bottles and the like.

The sleeve is preferably formed by a relatively rigid or hard plastic material, whereas the cap is preferably formed by a less rigid and more flexible material.

The cap may be connected to the sleeve or the catheter by means of a strap or a hinge 32. Preferably, the hinge is a so-called bi-stable living hinge, which exerts a force on the cap to swivel it out as soon as the cap has been released, and which maintains the cap in this swiveled out position. The swiveled out position may e.g. be at an angle exceeding 90 degrees as seen from the closed cap position, and preferably exceeding 120 degrees. The hinge ensures that the cap is at all times connected to the sleeve and catheter, and permit selectable movement of the cap between open and closed positions.

In the illustrative example, the hinge 32 is connected to an insert 33. The insert is here arranged to be fixedly connected to the sleeve. This fixed connection can be accomplished in various ways, such as by a friction fit, ultrasonic welding, mechanical locking, adhesive, etc. In the illustrative example, the sleeve is provided with an additional sidewall 24, arranged on one side of the sleeve body, and forming a double wall over a part of the sleeve, with a pocket 25 formed between the walls. Preferably, the additional sidewall 24 is arranged in such a way that the pocket 25 is opened towards the distal end, and closed at the proximal end of the sleeve. To this end, the additional side wall may taper towards the main body of the sleeve at the proximal side.

The pocket 25 is arranged to receive the insert 33 and engage it in a fixed connection. For example, as in the illustrative example, the insert may be provided with a tongue 34 having an outwardly protruding tip, and the additional sidewall 24 may be provided with a recess or opening 26 arranged to receive the tip of the tongue to form a snap-lock connection. However, other ways of forming mechanical connections may be used, as well as other types of connections.

The sleeve may have various cross-sectional shapes. In the illustrative example, the tubular compartment is essentially circular in cross-section, and with an outgrowth formed by the additional sidewall and the pocket formed therein.

The assembly further comprises a tubular case 4, having a closed proximal end 41, an open distal end 42, and a tubular sidewall 43 extending between the ends. The tubular case is arranged to receive at least the insertable section 11 of the catheter, and preferably also a part of the non-insertable section 12, and to accommodate these parts of the catheter during storage. The tubular case is arranged to be closed at the open distal end to form a sealed and sterile compartment for the accommodated catheter parts during storage. Closing and sealing of the open distal end 42 may be accomplished in various ways, such as by interaction and engagement with the catheter and/or the sleeve, and/or by use of additional closure and sealing elements.

In the illustrative example, the proximal part of the non-insertable section 12 of the of the catheter has a diameter and shape arranged to fit snugly within the opening 42 of the tubular case, thereby connecting the parts together, and wherein the gasket 16 provides a sealing of the compartment.

In addition, the tubular case 4 may be provided with mechanical connection elements to form a mechanical connection with corresponding mechanical connection elements in the sleeve 2. In the illustrative example, threads 45 are provided on an outer surface of the tubular case in the vicinity of the distal end opening, and arranged to releasably engage with corresponding internal threads (not shown) on the sleeve, in the vicinity of the proximal opening 22.

Hereby, a strong mechanical connection is established by the combination of the friction fit between the part of the catheter being inserted into the tubular case and the case wall and by the mechanical interconnection between the tubular case and the sleeve, and at the same time a sealed and sterile accommodation for the insertable part of the catheter is ensured by the gasket provided between the interior wall of the case and the inserted part of the catheter. Hereby, a very strong and reliable connection is formed, and at the same time enabling a thin and slender shape for the assembly.

However, naturally a gasket or the like may instead be arranged on the interior wall of the case, and other ways of ensuring a sterile and sealed environment may also be contemplated. Further, the connection between the sleeve and the tubular case may be accomplished in other ways, instead of using a threaded connection. For example, it may suffice to have a part of the tubular case extend into the sleeve, to form a friction fit.

Figure 1A:
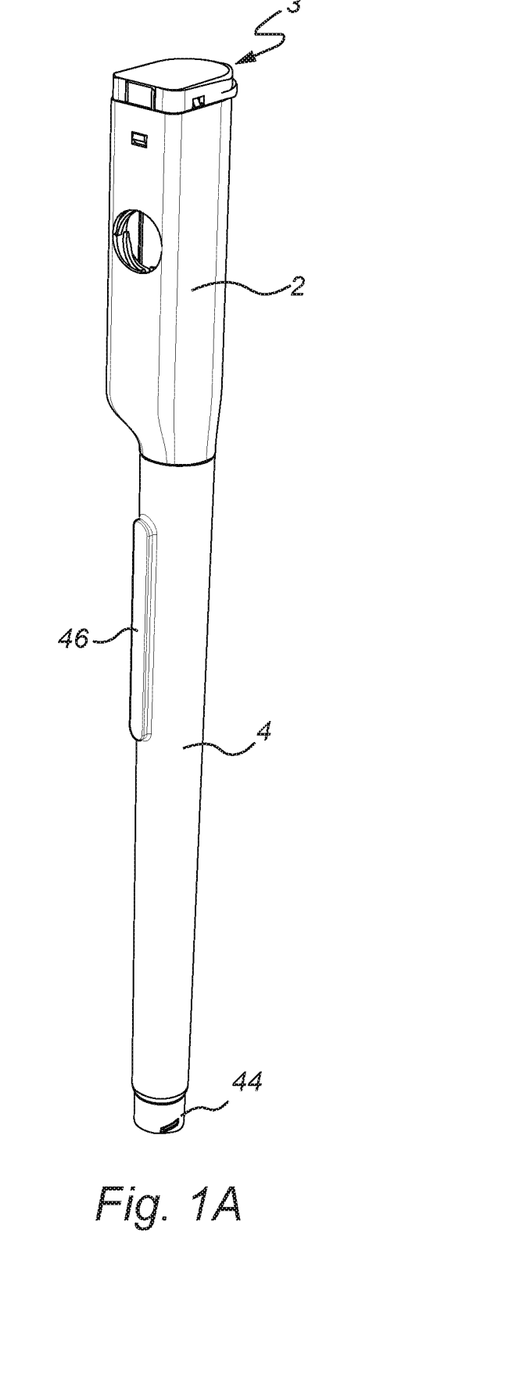
FIGS. 1A-1D are perspective views of a urinary catheter assembly in accordance with an embodiment of in a closed position, in an opened use position, and some intermediate positions between these end states.

Thus, in the closed storage position, as shown in FIG. 1A, the tubular case 4 forms a sterile and sealed compartment together with the cap 3, thereby maintaining the insertable part of the catheter, and here also the entire lumen of the catheter, clean and sterile during storage. Thus, no additional packages or the like are needed to maintain the assembly in a clean and sterile condition during storage and prior to use.

The threaded connection between the sleeve and the tubular case also, in addition to forming the mechanical interconnection, also provides an aid for separating the tubular case from the sleeve and catheter when the assembly is to be opened. By rotating the sleeve in relation to the tubular case, the threads will provide an axial movement between the tubular case and the sleeve, thereby forcing the sleeve and case apart. However, a similar opening action may also be provided in other ways. For example, the mating end surfaces of the sleeve and case may be arranged as sloped or curved surfaces, thereby also causing an axial movement between the parts upon rotation.

The tubular case is here illustrated as being essentially circular in cross-section, but other shapes, such as a rectangular or oval shape, may also be contemplated.

The tubular case is also provided with a second engagement member 44, to interact and engage with a first engagement member 27 provided on the sleeve. These engagement members allow the tubular case to be releasably connected to the sleeve in a second disposition, being different from the first disposition formed in the storage position. Hereby, the tubular case may, when in the second disposition, also functions as a handle, for allowing convenient and effective gripping and handling of the catheter during use. In this second disposition, the tubular case preferably assumes an angularly displaced position in relation to the longitudinal direction of the catheter and the sleeve, so that it extends laterally from the catheter, and may e.g. extend at about 90 degrees from the catheter/sleeve.

The first engagement member 27 is preferably arranged on the body portion 23 of the sleeve 2 at a distance from both the oppositely arranged openings 21, 22. In the illustrative example, the first engagement member 27 is arranged centrally on the sleeve body, but may additionally or alternatively be arranged close to one or both of the openings.

The second engagement member 44 is in the illustrative example arranged at the closed end 41 of the tubular case 4. However, additionally or alternatively, the second engagement member may be arranged at the open end of the tubular case, or be provided on the sidewall of the tubular case, between the ends 41, 42.

In the illustrative example, the first engagement member 27 is an opening or recess in the body portion of the sleeve 2, and the second engagement member 44 is a protrusion extending out from or being formed by the end of the tubular case 4. The second engagement member preferably has a form and shape complementary to the form and shape of the first engagement member, thereby allowing the first and second engagement member to mate and connect to each other.

In the illustrative example, the opening in the sleeve is provided in the additional sidewall 24, and also extends into a corresponding opening or recess 34 in the insert 33. Thus, in this example, the first engagement member is formed both by the opening in the sidewall and the opening or recess 34 in the insert 33.

However, alternatively the sleeve may be provided with a protrusion, arranged to be received by a corresponding opening in the tubular case.

Figure 4A:
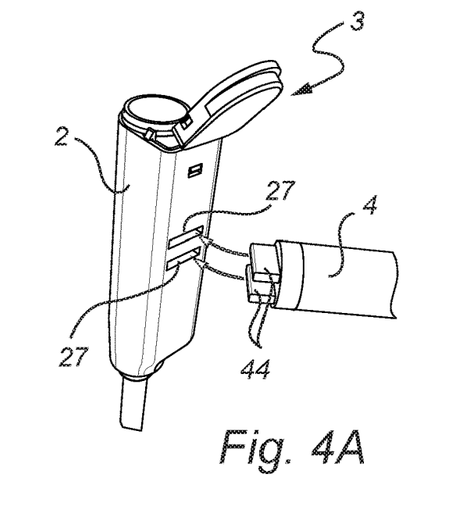
FIG. 4A-E schematically illustrate alternative types of engagement members to connect the tubular case and the sleeve together in the second, use disposition.
Figure 4B:
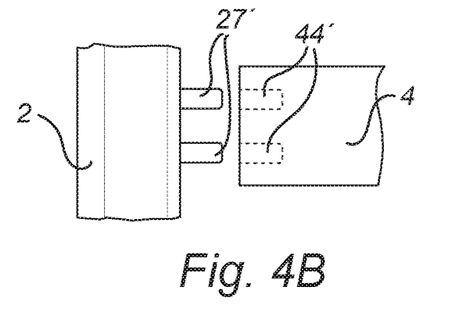

Also, more than one recess/opening and more than one protrusion may be provided, such as a two or three protrusions, arranged to be received in two or three corresponding openings, in a plug-and-socket type of connection. Such an embodiment is schematically illustrated in FIG. 4A, where the sleeve 2 is provided with two openings 27, and the tubular case 4 is provided with two protruding elements 44. More than two openings and protruding elements may also be used. Similarly, openings 44' may instead be formed in the tubular case, and corresponding protrusions 27' formed in the sleeve, as illustrated in FIG. 4B. It is also possible to provide a combination of one or more openings/recesses and one or more protruding elements on each of the sleeve and the tubular case.

Figure 2:
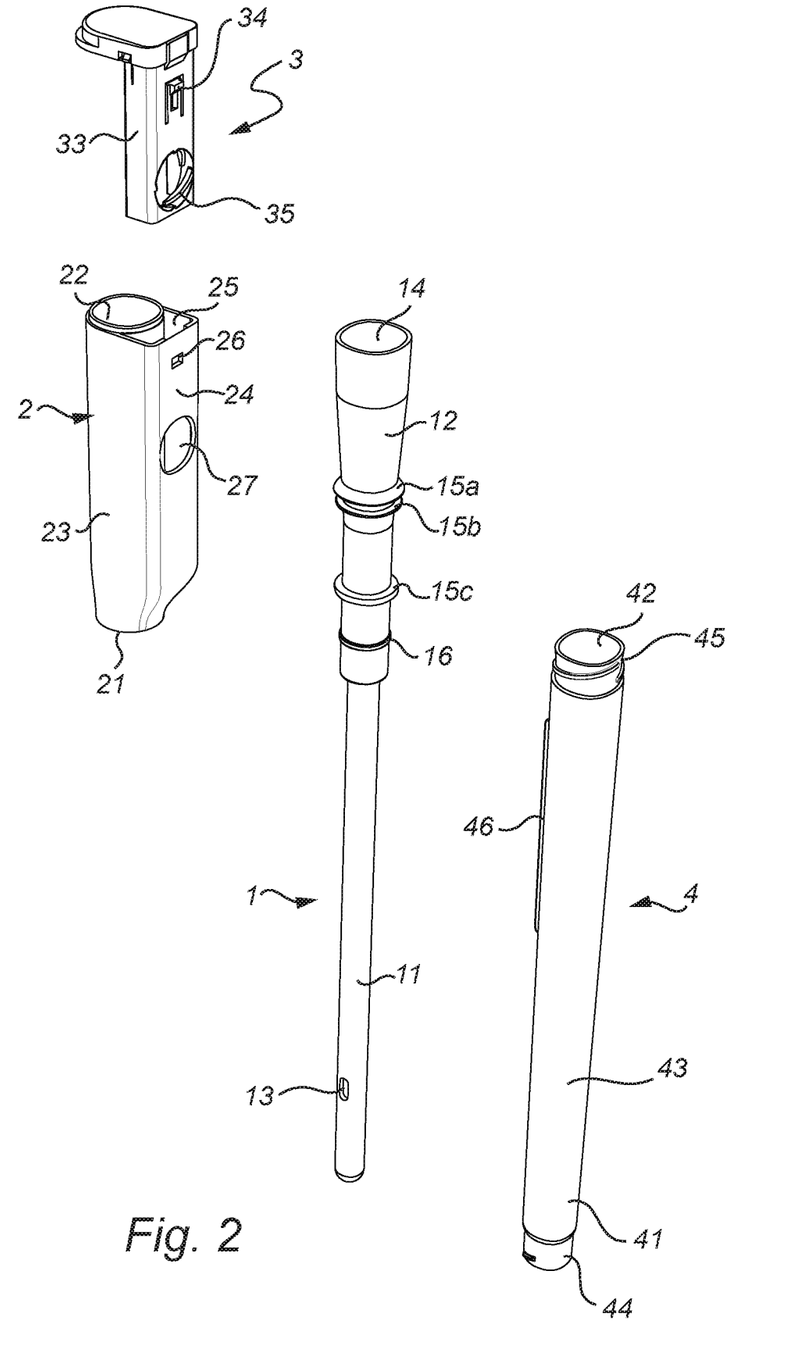
FIG. 2 is an exploded view of the urinary catheter assembly of FIG. 1.

In order to provide an improved mechanical interconnection, the protruding element 44 may, as shown in e.g. FIG. 2, be provided with external threads, and the opening/recess formed in the sleeve may be provided with corresponding internal threads. Hereby, the tubular case may be rotated into a strong mechanical interconnection.

However, it may also suffice with a friction fit between the protruding part(s) and the receiving opening(s)/recess(es). To obtain a stronger interconnection and easier mounting, the protruding part(s) may in this case be slightly conical or tapering, and the opening/recess may have a corresponding shape.

Figure 4C:
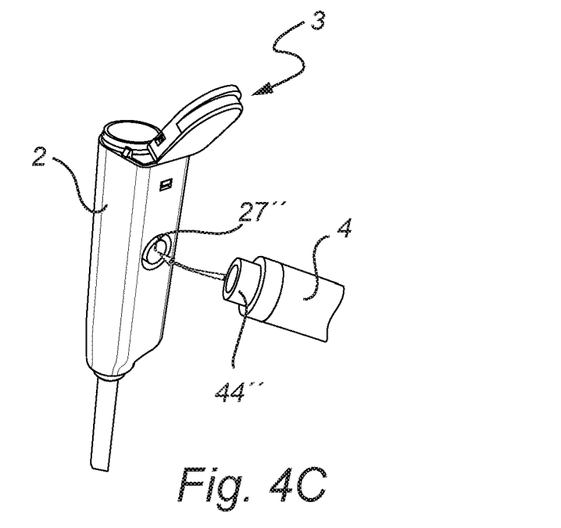

Additionally or alternatively, it is possible to have a protrusion 44" in the form of a ring or the like, as shown in FIG. 4C, and the opening 27" may be formed as an annular recess. Hereby, the protruding ring will be held more firmly in place, by the friction working on both the internal and external side thereof.

Figure 4D:
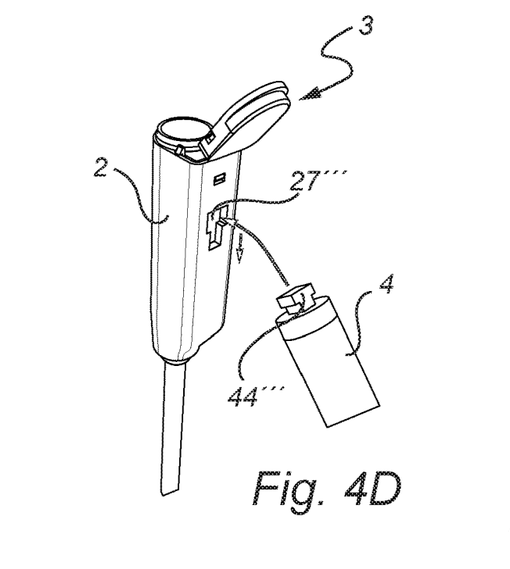

However, other types of engagement members are also feasible. As one example, illustrated in FIG. 4D, the protrusion 44''' is in the form of a latch, preferably with an undercut to form a tab, provided on one of the sleeve and the tubular case, and a corresponding slot opening 27''' is arranged on the other of the sleeve and the tubular case, wherein the latch and the slot are engageable with one another. In use, the protruding tab may hereby be inserted at the enlarged rearward part of the opening, and be pushed upwards, to be inserted into a narrower section with an undercut, thereby fixating the parts together.

Figure 4E:
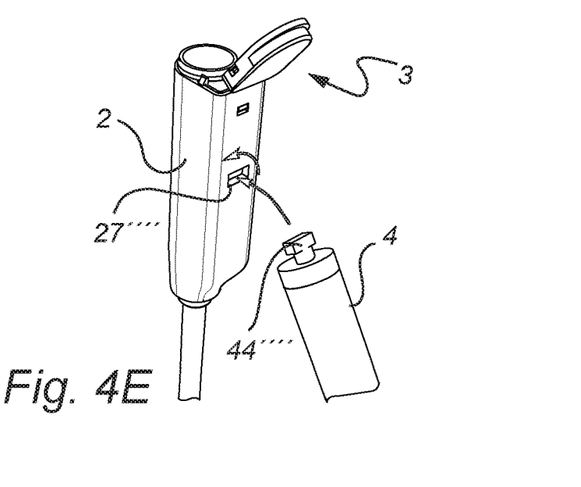

Similarly, as illustrated in FIG. 4E, the tab may be in the form of a wing, extending in two opposite directions, and the opening may be an elongate opening, sized to receive the tabs, and with an undercut towards one or both sides. In this arrangement, the protrusion may be inserted into the elongate opening, and then rotated in one direction to lock the parts together.

Many other alternatives for engaging the first and second engagement member are naturally feasible, as would be appreciated by the skilled reader.

Preferably, the first and second engagement members may be connectable through one of threads, a friction fit, a snap-lock and a snap-fit arrangement, and the first and second engagement members are preferably complementary to each other in shape and/or size, thereby enabling engagement between the members.

It is also feasible that the first and second engagement members are such that engagement in more than one way is possible, e.g. allowing the tubular case to be engaged in two or more different angular positions in relation to the sleeve. It is also possible to provide two or more first engagement members on the sleeve, each providing a different angular orientation of the tubular case when connected to the sleeve.

The tubular case 4 may further be provided with an elongate protrusion 46 extending out from the surface wall and extending generally in the length direction of the tubular case. The protrusion may e.g. be in the shape of a ridge, a rib, a fin or the like. Preferably, the protrusion only extends over a limited part of the length of the tubular case. However, the protrusion may alternatively extend over a substantial part of the length of the tubular case, or along the entire length. The protrusion serves multiple purposes. Firstly, the protrusion hinders the tubular case from rolling away e.g. when laid on a table, on the floor or the like. It also facilitates opening of the catheter assembly, and in particular the separation of the tubular case from the sleeve, since it makes it easier to grip and hold the tubular case. Still further, the projection indicates a direction, which is useable when the tubular case is attached in the second disposition. The projection may e.g. be directed towards the insertable end of the catheter when attached to the sleeve in the second disposition. The projection provides a both visibly and tactility recognizable reference direction, which aids the user in manipulating the catheter during catheterization, and in particular when the catheter is held in such a way that the catheter shaft is difficult to see for the user.

The projection may also assume other shapes, such as being a set of shorter, point-like protrusions and the like. Similar advantages can also to some extent be obtained by providing the tubular case with a non-circular outer cross-sectional shape, such as being oval, hexagonal, triangular, or the like.

In use, as illustrated in FIGS. 1A-1D, the urinary catheter assembly is first provided in a storage position, as illustrated in FIG. 1A, where the tubular case 4 is provided in the first disposition, and where the cap 3 is closed, thereby forming a closed and sealed compartment for the insertable part of the catheter.

Figure 1B:
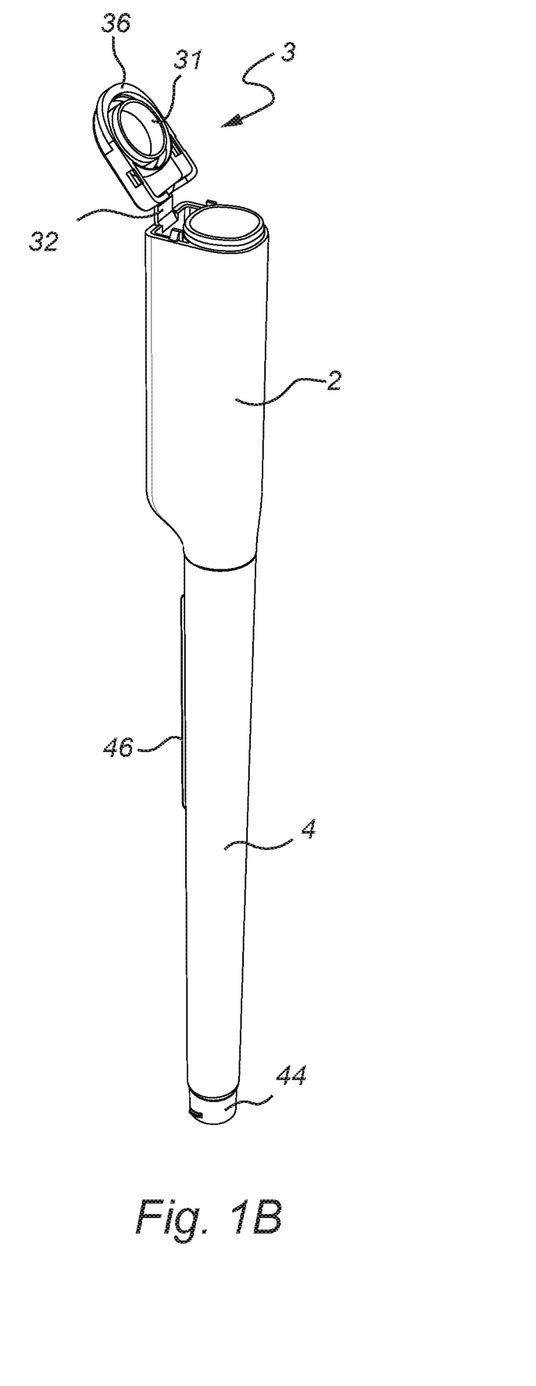

In preparation for use, the cap 3 may first be opened, as illustrated in FIG. 1B. However, this step of opening the cap may also be performed later, such as immediately prior to catheterization, or even after insertion of the catheter into the urethra.

Figure 1C:
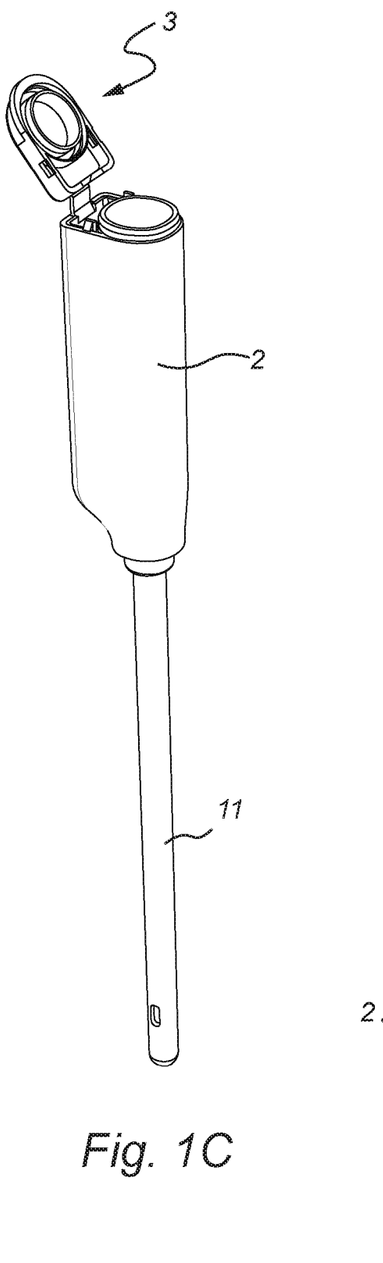
Figure 1D:
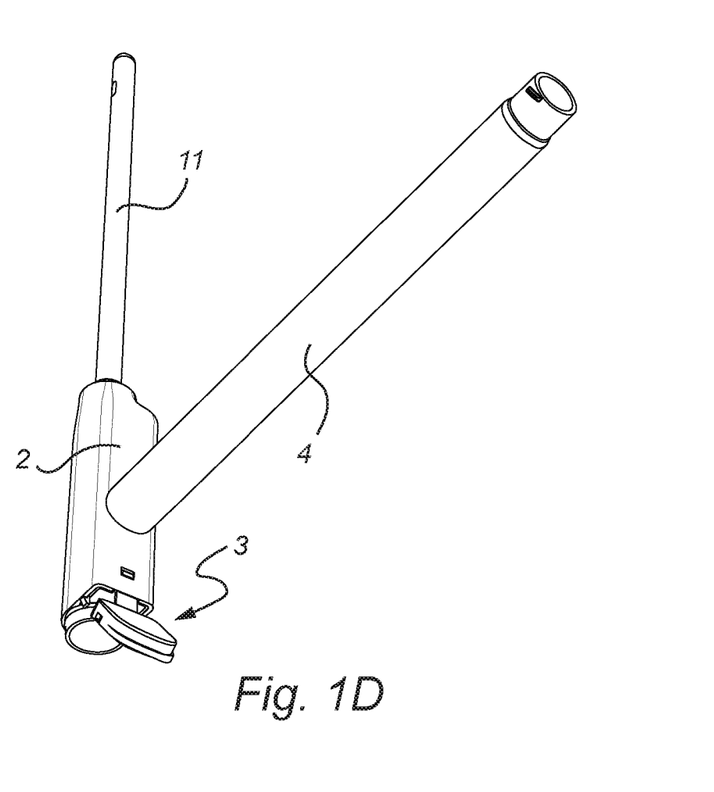

The tubular case 4 is then disconnected from the sleeve 2, by rotating the tubular case and the sleeve in relation to each other, and the catheter is extracted. This is illustrated in FIG. 1C. The catheter may now be used for catheterization. However, advantageously, the tubular case is first again connected to the sleeve, but now in the second disposition, by engaging the first and second engagement members. This state is illustrated in FIG. 1D. In this state, the tubular case extends laterally as a gripping member or handle, which may be used for manipulation of the catheter during the catheterization.

During catheterization, the urine may be drained directly from the outlet opening of the catheter and into a toilet bowl. However, it is also possible to connect an extension tube or urine collection bag to the funnel shaped outlet opening.

After catheterization, the catheter can be reassembled into the closed storage position, essentially by performing the preparation steps in the reverse order. Once the catheter is reinserted into the tubular case and the cap is reclosed, the package will retain all or at least some of its original sealing qualities, and will consequently not leak and protect the user from spillage and contamination.

A label that breaks upon opening, or other types of tamper proof, may be provided to make it easy to see if a urinary catheter assembly has been opened or used.

For producing and assembling the urinary catheter assembly, the sleeve 2, the tubular case 4, the cap 3 and the catheter 1 may each be produced and provided separately, as shown in the exploded view in FIG. 2.

The catheter can e.g. be produced in a conventional way, using conventional manufacturing equipment. The catheter can be produced by any biocompatible polymeric material having sufficient stiffness and flexibility, as is per se well known in the art.

The sleeve and tubular case are preferably formed by relatively hard plastic material, such as HDPE, nylon or polypropylene, and may e.g. be produced by injection molding. The sleeve and tubular case may further be produced by a non-transparent and opaque material, such that the contents cannot be easily identified.

The cap is preferably formed of a relatively less hard and more flexible material, and may also be produced e.g. by injection molding.

Figure 3A:
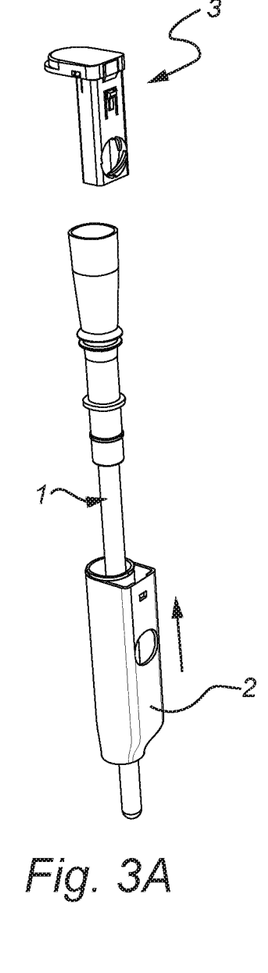
FIGS. 3A-3C show various stages in the assembly process for production of the urinary catheter assembly of FIG. 1.

For assembling the urinary catheter assembly, the sleeve 2 may first be fixedly connected to the catheter 1, as shown in FIG. 3A. This fixed connection may e.g. be achieved by simply pulling the sleeve into place over the catheter, to form a friction fit, and snap-lock interconnection or the like. However, it may also involve adhesion, ultrasonic welding or other measures to ensure a strong connection.

Figure 3B:
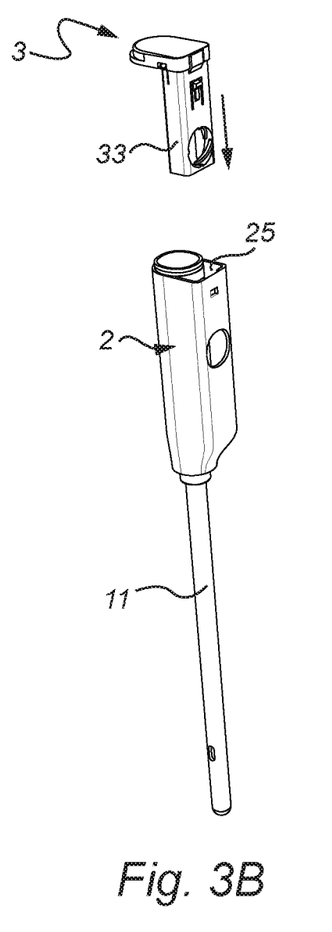

The cap 3 is then arranged on the sleeve, as illustrated in FIG. 3B. The insert 33 is hereby pushed into place in the pocket 25, and fixedly connected. This fixed connection may e.g. be achieved by simply pushing the insert into the pocket, to form a friction fit, and snap-lock interconnection or the like. However, it may also involve adhesion, ultrasonic welding or other measures to ensure a strong connection. The cap may then be rotated to close the catheter lumen.

Figure 3C:
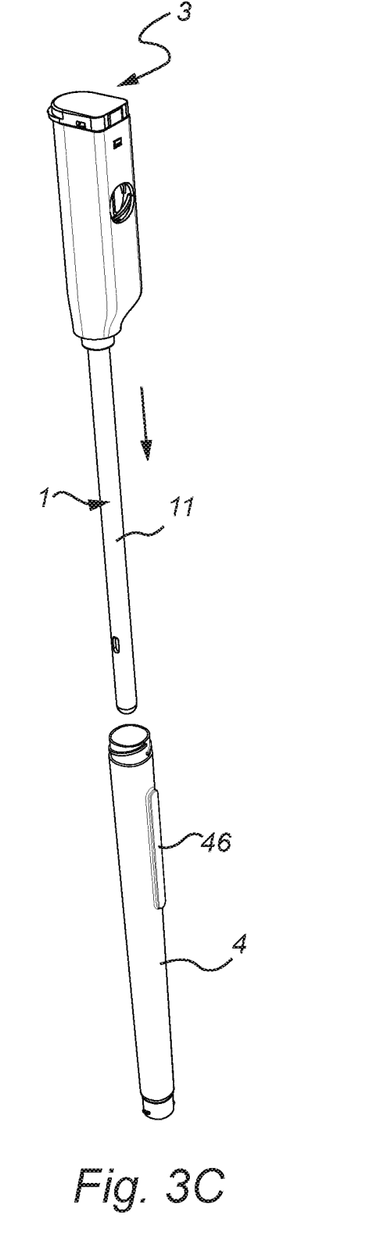

The catheter, now with the sleeve and cap attached, is then inserted into the tubular case 4, and are secured in place, e.g. by rotating the parts into a threaded interconnection.

However, as an alternative, it may also be possible to assemble two or more of the components already during manufacturing of the parts, e.g. by use of two-shot molding processes or the like. For example, it may be possible to produce the sleeve and cap as a single unit by such a method.

The assembly is then sterilized and ready for use.

In case a hydrophilic catheter is used, the urinary catheter assembly may also comprise a wetting fluid. However, the wetting fluid for activation of the catheter need not be provided within the package. Instead, a wetting fluid may be poured into the package after opening of the package, for wetting of the catheter while it still remains in the package. In some occasions, the catheter may even be removed from the package and wetted e.g. in a different container, even though this is normally not preferred.

However, preferably the wetting fluid is arranged within the package, so that the hydrophilic surface of the catheter can be activated even before opening of the package. In one embodiment, the wetting fluid is arranged separated from the catheter, in a wetting fluid container (not shown), such as a pouch or a sachet. The wetting fluid container is openable by means of e.g. exerting a pressure to the container, whereby the wetting fluid is released into the package, thereby wetting the hydrophilic surface of the catheter. The wetting fluid container may also be arranged to open automatically when the catheter assembly is opened, e.g. by the opening of the cap or the rotation of the tubular case in relation to the sleeve. In another embodiment, the wetting fluid is arranged directly in the compartment of the package which also houses the catheter, so that the hydrophilic surface of the catheter is in direct contact with the wetting fluid during storage, and thereby is maintained in an activated, ready-to-use state.

The wetting fluid is preferably a liquid, and most preferably an aqueous liquid, such as water or saline. However, the wetting fluid may also be a gas, providing a moist atmosphere in the package sufficient for activation of the hydrophilic surface. Thus, the wetting fluid may be any fluid, gas or liquid, that wets/activates a hydrophilic surface of the catheter.

In case a non-hydrophilic catheter is used, the urinary catheter assembly may comprise a supply of lubricant, such as a compartment arranged overlying the catheter shaft, so that the shaft is lubricated while being pulled out from the tubular case.

Specific embodiments of the invention have now been described. However, several alternatives are possible, as would be apparent for someone skilled in the art. For example, although the wetting fluid in the described embodiments is arranged in direct contact with the catheter, but may alternatively be arranged separated from the catheter, in a wetting fluid container. Further, it is possible to use many different types of engagement members for attaching the tubular case to the sleeve for use as a handle. The cap may similarly be designed and shaped in various ways, and need e.g. not be connected by a hinge. Also, the cap can also be omitted, and instead be replaced by a foil cover, a breakable membrane, a dissolving closure or the like. Such and other obvious modifications must be considered to be within the scope of the disclosed embodiments, as it is defined by the appended claims. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements. Further, a single unit may perform the functions of several means recited in the claims.

The invention claimed is:

1. A urinary catheter assembly comprising:
   a urinary catheter including an insertable section and a non-insertable section;
   a tubular case provided with a closed end and an open end; and
   a sleeve fixedly arranged over at least a part of the non-insertable section of the urinary catheter, the sleeve including two oppositely arranged openings and a body portion extending between said openings;
   wherein the non-insertable section of the catheter includes a flared connector portion, wherein the flared connector portion is at least partly accommodated within the sleeve,
   wherein the tubular case, in a storage position, is arranged to enclose the insertable section of the urinary catheter and removably connected to one or both of the sleeve or the non-insertable section of the urinary catheter, wherein the tubular case is in a first disposition in relation to the sleeve, and
   wherein the body portion of the sleeve includes a first engagement member, and wherein the tubular case includes a second engagement member, thereby enabling the tubular case, when removed from the non-insertable section of the urinary catheter, to be releasably connected to the sleeve in a second disposition, the second disposition being different from the first disposition.

2. The catheter assembly of claim 1, wherein the flared connector portion has a length exceeding a length of the sleeve.

3. The catheter assembly of claim 1, wherein the flared connector extends out from the sleeve through at least one of the two oppositely arranged openings.

4. The catheter assembly of claim 1, wherein the first engagement member is arranged on the body portion of the sleeve at a distance from both said oppositely arranged openings.

5. The catheter assembly of claim 1, wherein the first engagement member is at least one of an opening or recess in the body portion of the sleeve and a protrusion extending out from the body portion of the sleeve.

6. The catheter assembly of claim 1, wherein the first and second engagement members are connectable through one of threads, a friction fit, a bayonet mount, a Luer connection, a snap-lock or a snap-fit arrangement.

7. The catheter assembly of claim 1, wherein the tubular case, when connected to the sleeve in the second disposition, extends at an angle from a longitudinal direction of the sleeve.

8. The catheter assembly of claim 7, wherein the angle from the longitudinal direction of the sleeve is in the range of 60-120 degrees.

9. The catheter assembly of claim 7, wherein the angle from the longitudinal direction of the sleeve is in the range of 75-105 degrees.

10. The catheter assembly of claim 1, further comprising an openable cap for closing a release opening at the non-insertable section of the urinary catheter.

11. The catheter assembly of claim 10, wherein the cap is connected to one or both of the sleeve or the non-insertable section of the catheter via a hinge.

12. The catheter assembly of claim 1, wherein the second engagement portion is arranged at the closed end of the tubular case.

13. The catheter assembly of claim 1, wherein the tubular case comprises a sloped or curved surface, and the sleeve comprises a correspondingly sloped or curved surface which mates with the sloped or curved surface of the tubular case when in the storage position.

14. The catheter assembly of claim 1, wherein the insertable section of the catheter comprises a hydrophilic surface, and wherein the catheter assembly further includes a wetting fluid for wetting of said hydrophilic surface.

15. The catheter assembly of claim 1, wherein the tubular case together with the non-insertable section provides a sterile and moisture proof compartment for the insertable section of the catheter in the first disposition.

16. A method for producing a urinary catheter assembly comprising:
    providing a urinary catheter including an insertable section and a non-insertable section;
    fixedly arranging a sleeve over the non-insertable section; and
    arranging at least the insertable section in a tubular case;
    wherein the tubular case, in a storage position, is removably connected to one or both of the sleeve or to the non-insertable section of the urinary catheter, wherein the tubular case is in a first disposition in relation to the sleeve, and wherein the sleeve includes a first engagement member, and wherein the tubular case includes a second engagement member, thereby enabling the tubular case, when removed from the non-insertable section of the urinary catheter, to be releasably connected to the sleeve in a second disposition, the second disposition being different from the first disposition, wherein the second engagement portion is arranged at a closed end of the tubular case.

17. A method for preparing a urinary catheter assembly for use, the catheter assembly including a urinary catheter with an insertable section and a non-insertable section, a tubular case provided with a closed end and an open end, and a sleeve fixedly arranged over at least a part of the non-insertable section of the urinary catheter, the sleeve including two oppositely arranged openings and a body portion extending between said openings, the tubular case, in a storage position, is arranged to enclose the insertable section of the urinary catheter and removably connected to one or both of the sleeve or the non-insertable section of the urinary catheter, the tubular case being in a first disposition in relation to the sleeve, the body portion of the sleeve including a first engagement member, the tubular case including a second engagement member to enable the tubular case, when removed from the non-insertable section of the urinary catheter, to be releasably connected to the sleeve in a second disposition different from the first disposition, the method comprising:
    removing the insertable section from the storage position in the tubular case;
    bringing the assembly from the first disposition to the second disposition;
    connecting, releasably, the first engagement member of the sleeve with the second engagement member of the tubular case; and
    using the tubular case as a handle for manipulation of the catheter when in the second disposition, wherein the second engagement portion is arranged at the closed end of the tubular case.

18. A urinary catheter assembly comprising:
    a urinary catheter having an insertable section and a non-insertable section;
    a tubular case provided with a closed end and an open end; and a sleeve fixedly arranged over at least a part of the non-insertable section of the urinary catheter, the sleeve including two oppositely arranged openings and a body portion extending between said openings;

wherein the tubular case, in a storage position, is arranged to enclose the insertable section of the urinary catheter and removably connected to the sleeve and/or to the non-insertable section of the urinary catheter, wherein the tubular case is in a first disposition in relation to the sleeve, and wherein the body portion of the sleeve is provided with a first engagement member, and wherein the tubular case is provided with a second engagement member, thereby enabling the tubular case, when removed from the non-insertable section of the urinary catheter, to be releasably connected to the sleeve in a second disposition, the second disposition being different from the first disposition, wherein the second engagement portion is arranged at the closed end of the tubular case.

\* \* \* \* \*